United States Patent [19]

Bardoux et al.

[11] Patent Number: 4,538,071
[45] Date of Patent: Aug. 27, 1985

[54] PRACTICAL DEVICE FOR THE MEASUREMENT OF THE ABSORBED DOSE VERSUS DEPTH IN SOFT TISSUES

[75] Inventors: Raymond Bardoux, Neuilly; Henri Joffre, Bourg-la-Reine, both of France

[73] Assignees: Commissariat a l'Energie Atomique; Merlin Gerin, both of France

[21] Appl. No.: 435,330

[22] Filed: Oct. 19, 1982

[30] Foreign Application Priority Data

Oct. 27, 1981 [FR] France ................................ 81 20282

[51] Int. Cl.³ ............................................ G01D 18/00
[52] U.S. Cl. ................................ 250/505.1; 250/252.1; 378/157
[58] Field of Search .................. 378/207, 18, 156–159; 250/252.1, 505.1

[56] References Cited

U.S. PATENT DOCUMENTS 3,867,638 2/1975 Golden ................................ 378/207
4,163,152 7/1979 Suzuki ................................ 378/18
4,181,858 1/1980 Moore ................................ 378/159

FOREIGN PATENT DOCUMENTS 26880 3/1964 Fed. Rep. of Germany ...... 378/159
1041354 9/1966 United Kingdom .

OTHER PUBLICATIONS

Health Physics, vol. 24, Jan. 1973, Pergamon Press, pp. 53–58.
Nuclear Instr. & Methods, vol. 147, (1977), pp. 119–123.
Health Physics, vol. 31, Aug. 1976, Pergamon Press, pp. 97–108.

Primary Examiner—Alfred E. Smith
Assistant Examiner—Carolyn E. Fields
Attorney, Agent, or Firm—Parkhurst & Oliff

[57] ABSTRACT

The present invention relates to a device for measuring the effective dose. In a preferred embodiment, the device includes a detector located in a cavity accommodated in the periphery of an inner cylinder which is eccentrically mounted in a right cylinder. The diameter of the right cylinder is close to twice the diameter of the eccentric cylinder and the cylinders are driven in rotation to set a rectilinear displacement to the cavity. The device can be used to determine the variation of the absorbed dose rate versus depth.

5 Claims, 4 Drawing Figures

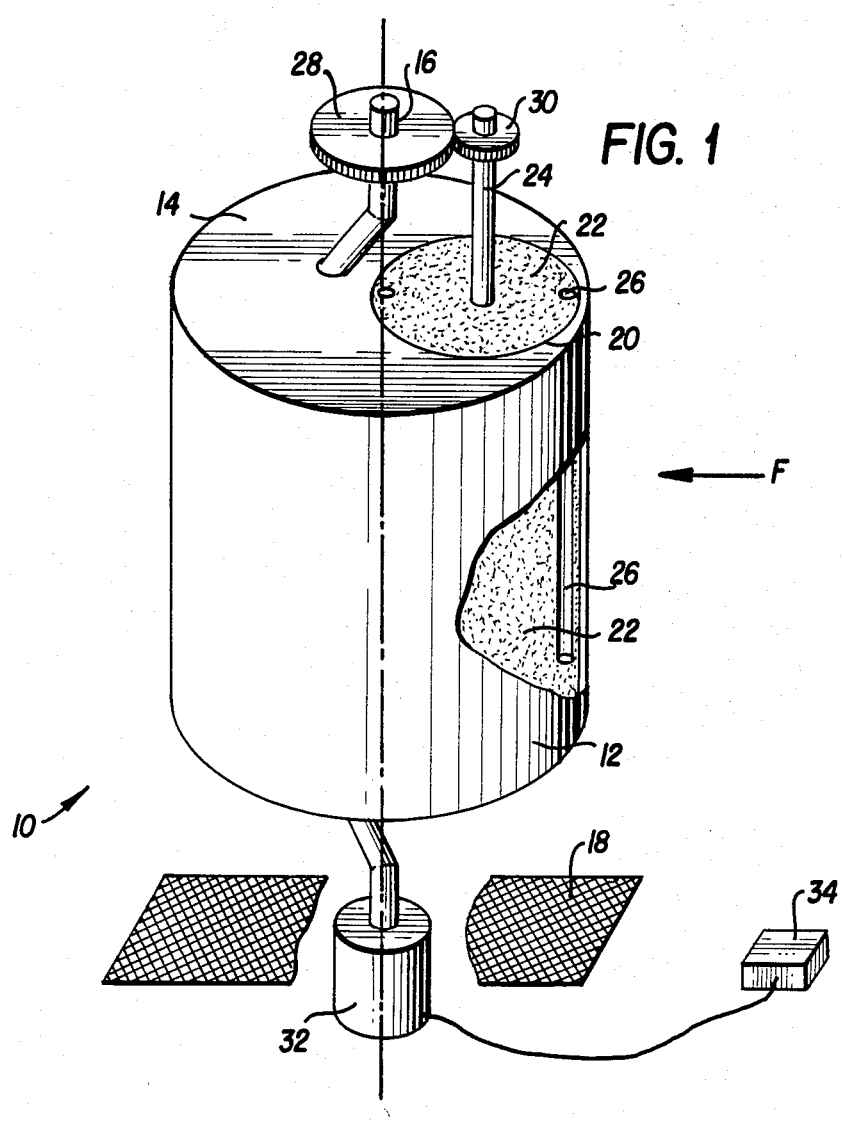
FIG. 1
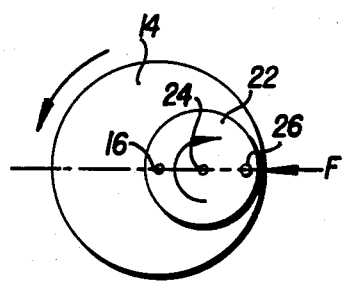
FIG. 2
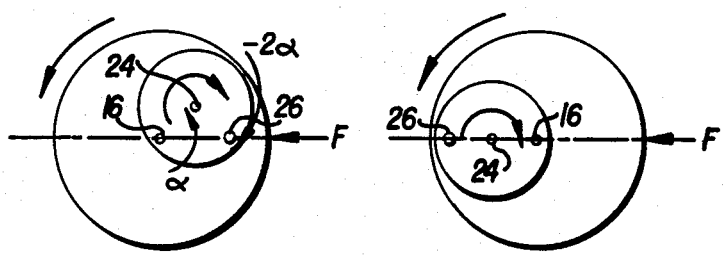
FIG. 3
FIG. 4

PRACTICAL DEVICE FOR THE MEASUREMENT OF THE ABSORBED DOSE VERSUS DEPTH IN SOFT TISSUES

BACKGROUND AND SUMMARY OF THE INVENTION

The invention relates to a device of irradiation measurement comprising a phantom made of a material equivalent to the system soft tissues showing a cavity for housing a radiation detector.

A directive of the Euratom Council determines the basic standards relative to the sanitary protection of the population and the workers against the dangers resulting from ionizing radiations. This directive paints out the ideas of effective dose and dose index, the effective dose being the sum of dose positional mean equivalents in the different organs or tissues, and the dose index being the equivalent of the maximum dose in the middle volume of a 30 cm diameter sphere made of a material equivalent to soft tissues with a volume mass of 1 g per $cm^3$. An index of deep dose equivalent and an index of surface dose equivalent are distinguished and if the new dose limits to be abided for the workers or the public are established in terms of effective dose, these dose limits are considered as abided if the index of deep dose equivalent does not exceed the stated limit for the effective dose and if the index of surface dose equivalent does not exceed the stated dose limit for the skin.

The practical devices actually available do not meet the aims stated by the above-mentioned requirements. An object of the present invention is to permit the realization of a measuring device allowing the practitioner of the radioprotection close to the nuclear or radiation generating plants to determine rapidly and conveniently under all circumstances the variation of the absorbed dose rate versus depth in a phantom simplified and made of a material equivalent to the system soft tissues concerning the interactions of electrons, photons and neutrons with the matter.

According to the present invention the measuring device is characterized in that the phantom includes a first rotary right cylinder having a cylindrical housing with an axis parallel and eccentric relative to the axis of the first cylinder, and a second revolution cylinder mounted in rotation with weak play in the cylindrical housing, the cavity being eccentrically accommodated in the second cylinder, so that the combined rotations of the first and second cylinders make the depth of the detector vary in the phantom according to the diameter of a circle of the first cylinder.

The theoretical use of a 30 cm diameter sphere for these measurements shows the disadvantages to be of a not very convenient realization and working, and according to the present invention, the sphere is advantageously replaced by a right cylinder 30 cm in diameter and 30 cm in height allowing the required measurements with a largely sufficient approximation. The second cylinder of same height and with a diameter close to 15 cm is eccentrically disposed within the first cylinder. The two cylinders have parallel axes and are actuated with rotation motions in opposite direction, the rotation angle of the first cylinder being half of the rotation angle of the second cylinder. It will appear from the following description that the device with eccentric cylinders according to the invention permits to displace the cavity and the detector located in the cavity according to a diameter of the first cylinder, this displacement being able to be at constant speed if one takes care in modulating the rotation speeds of the cylinders. The device can then provide the direct recording of the variation of the absorbed dose versus depth when it is a unidirectional or isotropic irradiation. The rotation motion of the second cylinder is advantageously derived from the one of the first cylinder, for example by a mechanical connection with gearing, every other drive device being of course usable. The rotation of the first cylinder can be automatically realized by a motor controlled by a logic system with wired memory and with a selective time base allowing different transit times with uniform speed of the cavity. The simultaneous recording of the dose rate in the detecting cavity permits a direct indication and a recording of the variation of this dose rate versus depth in the phantom.

BRIEF DESCRIPTION OF THE DRAWINGS

Other advantages and technical data will more clearly appear from the following description, wherein reference is made to the accompanying drawing, in which:

FIG. 1 is a perspective schematic view, partially cut-away, of a measuring device according to the invention;

FIGS. 2, 3 and 4 are plan schematic views of eccentric cylinders, respresented in different successive positions, of the device according to FIG. 1.

DETAILED DESCRIPTION OF THE PREFERRED EMBODIMENT

On the Figures, a measuring device, designated by the general mark 10, includes a cylindrical phantom 12 made of a material equivalent to the system soft tissues concerning the interactions of electrons, photons and neutrons with the matter. The material can be of the type described in French Pat. No. 77 27679, registered Sept. 7, 1977, the composition of this material being able to be modified to abide by the different regulations. The phantom 12 is constituted by a first right cylinder 14, the shaft 16 of which is mounted for rotation on a fixed support 18. The first right cylinder 14 has a cylindrical housing 20 with its axis parallel to the shaft or axis 16 of the first cylinder 14. A second right cylinder 22 of the same height as the first cylinder 14 is mounted for rotation with weak play in the housing 20. The diameter of the second cylinder or inner cylinder 22 is approximately equal to half of the diameter of the first cylinder 14 and the spacing between the axis 24 of the inner cylinder 22 and the axis 16 of the first cylinder 14 is slightly equal to the radius of the inner cylinder 22. This data leads to the conclusion that the eccentric inner cylinder 22 is slightly tangent internally to the right cylinder 14. The height and diameter of the phantom are close to 30 cm, the diameter of the inner cylinder 22 being in this case close to 15 cm. The inner cylinder 22 includes a cavity 26 extending along a generator of the cylinder parallel to the axis 24. In the cavity 26 is located a radiation detector (not represented) of any type well-known to the specialists. The cavity 26 opens on the upper head of the phantom 12, this cavity extending for example on half height, so as to position the detector in the middle of the phantom 12 height.

By making the first cylinder 14 and/or the inner cylinder 22 turn, the position of the cavity 26 within the phantom 12 can be modified. In the case represented on the Figures of an unidirectional irradiation, represented by the arrow F, the material thickness having to be crossed by this radiation to reach the cavity 26 can be modified. In position of the cylinders 14, 22 represented on FIGS. 1 and 2, the cavity 26 is adjacent to the outer surface of the phantom 12 struck by the radiation F. The depth of the cavity 26 within the phantom 12 is minimum, this minimum value being determined by the constructive characteristics of the apparatus. On FIG. 2, the axes 16,24 are aligned with the cavity 26 in direction of the radiation F. By making the first right cylinder 14 turn by an angle $\alpha$ and the inner cylinder 22 by an angle $-2\alpha$ the cavity 26 comes in an intermediate position represented on FIG. 3, remaining aligned with the radiation F. FIG. 4 represents the apparatus after a rotation of the first right cylinder 14 by 180° and a corresponding rotation of the inner cylinder 22 by 360°. The axes 16, 24 and the cavity 26 are still aligned with the radiation F, the cavity 26 being in position of maximum depth. It is easy to see that the rotation motion of the right cylinder 14, associated with a reverse rotation by a double angle of the inner cylinder 22, is transformed into an alternating rectilinear motion of the cavity 26. The rotation of the cylinders 14 can be manually accomplished, but it is advantageous to couple the cylinders 14, 22, for example mechanically to impose the double reverse rotation. A connection by toothed wheel 28 cottered on the shaft 16 and by pinion 30 cottered on the shaft 24 is schematically represented on FIG. 1. The diameter of the toothed wheel 28 is of course twice the one of the pinion 30 to accomplish the double angular rotation of the cylinder 22. The apparatus can be improved by coupling the shaft 16 to a drive motor 32 of any type, for example an electric motor step by step operated by a control equipment 34. It is understood that a drive with variable speed of the shaft 16 permits one to realize a uniform displacement of the cavity 26 versus time. The control equipment 34 can include for example a logic system with wired memory with a selective time base to realize a uniform speed of the cavity 26 displacement within the phantom 12, this uniform speed being adjustable. The uniform variation of depth versus time allows a measurement and a recording of the dose rate in the detecting cavity versus depth. According to the invention the performance of the measuring apparatus follows from the former description and it is enough to recall that it permits one to determine rapidly and without any risk of error the variation of the absorbed dose rate versus depth in a phantom 12. It is then possible to verify if the dose limits are abided under all circumstances.

Of course the invention is not at all limited to the embodiments more fully described and shown, but on the contrary it extends to any variant remaining in the limit of the equivalences, in particular to the one in which the inner cylinder 22 should be limited to a central disc incorporated in the right cylinder 14, or also to the one in which the rectilinear displacement of the cavity 26 should be imposed by guiding slides cooperating with a wrist carried by the inner cylinder 22.

What is claimed is:

1. A device for irradiation measurement comprising a phantom representing a portion of the human body and having a cavity for housing a radiation detector, the phantom comprising a first rotary right cylinder having a first axis and a cylindrical housing with a second axis parallel and eccentric relative to said first axis of the first cylinder, a second revolution cylinder mounted for rotation in said cylindrical housing, said cavity being eccentrically accommodated in said second cylinder, and drive means for rotating the second cylinder in an opposite direction and by a rotation angle twice the rotation angle of the first cylinder for varying the depth of the detector in the phantom.

2. The device according to claim 1, wherein said first and second cylinders are made of the same material.

3. The device according to claim 1, wherein the diameter of the first cylinder is substantially twice the diameter of the second cylinder, the second cylinder being substantially tangent to the first cylinder and the cavity being accommodated adjacent to the edge of the second cylinder.

4. The device according to claim 1, wherein the drive means rotates said first cylinder at a variable angular speed to linearly reciprocate the cavity at a substantially uniform speed.

5. The device according to claim 1, wherein the height of said cylinders is close to 30 cm, the diameter of the first cylinder is close to 30 cm and the diameter of the second cylinder is close to 15 cm.

* * * * *